(12) United States Patent
Shi et al.

(10) Patent No.: US 11,119,047 B2
(45) Date of Patent: Sep. 14, 2021

(54) SERS SUBSTRATE OF METAL-MODIFIED SEMICONDUCTOR-BASED BIONIC COMPOUND EYE BOWL STRUCTURE AND CONSTRUCTION METHOD

(71) Applicant: JIANGNAN UNIVERSITY, Wuxi (CN)

(72) Inventors: Gang Shi, Wuxi (CN); Ying Li, Wuxi (CN); Jie Chen, Wuxi (CN); Xuan Jin, Wuxi (CN); Likui Wang, Wuxi (CN); Dawei Wang, Wuxi (CN); Jingguo Yang, Wuxi (CN); Xinxin Sang, Wuxi (CN); Caihua Ni, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/082,894

(22) Filed: Oct. 28, 2020

(65) Prior Publication Data

US 2021/0109025 A1 Apr. 15, 2021

(30) Foreign Application Priority Data

Oct. 29, 2019 (CN) .......................... 201911038162.3

(51) Int. Cl.
*G01N 21/65* (2006.01)
*C23C 30/00* (2006.01)
*B82Y 30/00* (2011.01)
*B82Y 40/00* (2011.01)
(Continued)

(52) U.S. Cl.
CPC ........... *G01N 21/658* (2013.01); *C23C 30/00* (2013.01); *B82Y 30/00* (2013.01); *B82Y 40/00* (2013.01); *G01N 33/02* (2013.01); *G01N 33/18* (2013.01)

(58) Field of Classification Search
CPC ...... G01N 21/658; G01N 33/02; G01N 33/18; C23C 30/00; B82Y 20/00; B82Y 30/00; B82Y 40/00
See application file for complete search history.

(56) References Cited

PUBLICATIONS

Lee, Changwon, et al. "3D plasmonic nanobowl platform for the study of exosomes in solution." Nanoscale 7.20 (2015): 9290-9297. (Year: 2015).*

(Continued)

*Primary Examiner* — Robert J Eom
(74) *Attorney, Agent, or Firm* — CBM Patent Consulting, LLC

(57) ABSTRACT

The present invention discloses an SERS substrate of a metal-modified semiconductor-based bionic compound eye bowl structure and a construction method, and belongs to the technical field of nano materials. The present invention is based on a multi-time interface self-assembly method. Firstly, a small ball template is constructed by using a gas-liquid interface assembly process. Then, a semiconductor bowl structure array is induced to be formed by the template by using a solid-liquid interface assembly process. Next, a semiconductor bowl is assembled to a surface of a pyramid-shaped cone to form a bionic compound eye structure by using a transfer process. Finally, a surface of the bionic compound eye structure is modified with a layer of uniformly distributed metal particles by a physical deposition method or a chemical deposition method, thereby forming the SERS substrate of the metal-modified semiconductor-based bionic compound eye bowl structure.

8 Claims, 2 Drawing Sheets

(51) Int. Cl.
    *G01N 33/02*     (2006.01)
    *G01N 33/18*     (2006.01)

(56) References Cited

PUBLICATIONS

Das, Gobind, et al. "Large-scale plasmonic nanocones array for spectroscopy detection." ACS applied materials & interfaces 7.42 (2015): 23597-23604. (Year: 2015).*

* cited by examiner

SERS SUBSTRATE OF METAL-MODIFIED SEMICONDUCTOR-BASED BIONIC COMPOUND EYE BOWL STRUCTURE AND CONSTRUCTION METHOD

This application claims priority to Chinese Patent Application Ser. No. CN201911038162.3 filed on 29 Oct. 2019.

TECHNICAL FIELD

The present invention relates to an SERS substrate of a metal-modified semiconductor-based bionic compound eye bowl structure and a construction method, and belongs to the technical field of nano materials and nanochemistry.

BACKGROUND ART

A composite material with a specific structure is designed by compounding single nano materials, so that the composite material has intrinsic performance, and is also endowed with new special functions. By regulating and controlling the material in this mode, the performance limitation of a single-component material is broken through, and excellent application prospects are realized in the aspects of development of functional new materials, effective utilization of energy, pollution treatment and function detection. A bionic nano structure plays an important role in preparing nano composite materials, such as trace sensors, flat panel displays, self-cleaning color-changing glass and solar cells. These bionic micro-nano structures can effectively improve the mechanical, optical and electrical performance. Particularly in the field of SERS detection, a host metal material is compounded with a photocatalytic material, such as $TiO_2$, graphene, ZnO and $Cu_2S$, the Raman signal amplification is realized, and the requirements of long-term use are met. However, these compounding processes only focus on simple compounding of materials, and ignore the structure design in a composite material assembling process, so that the comprehensive performance of the SERS substrate in practical application is greatly compromised, and this problem needs to be solved.

SUMMARY OF THE INVENTION

In order to solve the technical problem, the present invention is based on a multi-time interface self-assembly method. Firstly, a small ball template is constructed by using a gas-liquid interface assembly process. Then, a semiconductor bowl structure array is induced to be formed by the template by using a solid-liquid interface assembly process. Next, a semiconductor bowl is assembled to a surface of a pyramid-shaped cone to form a bionic compound eye structure by using a transfer process. Finally, a surface of the bionic compound eye structure is modified with a layer of uniformly distributed metal particles by a physical deposition method or a chemical deposition method, thereby forming the SERS substrate of the metal-modified semiconductor-based bionic compound eye bowl structure. The whole process is simple and easy to implement. The SERS substrate of the present invention is a highly sensitive, renewable and reusable active substrate due to its special bionic structure and the special properties of a semiconductor material.

A first objective of the present invention is to provide an SERS substrate of a metal-modified semiconductor-based bionic compound eye bowl structure. The SERS substrate includes a cone-shaped structure substrate, a semiconductor bowl coating a surface of the cone-shaped structure substrate, and metal particles uniformly modifying a surface of the semiconductor bowl. The semiconductor bowl is of a continuously and closely arranged single-layer bowl structure. A height of the semiconductor bowl is 0.01-10 μm, and a bowl opening diameter of the semiconductor bowl is 0.01-10 μm. The cone is a micron pyramid cone, and a height of the micron pyramid cone is 1-100 μm. A particle size of the metal particles is 1-100 nm.

Further, a material of the semiconductor bowl is silicon, metal oxide, metal sulfide, metal phosphide or a conductive polymer.

Further, a material of the metal particles is one or more of gold, silver, palladium, platinum, copper, lithium or sodium.

Further, a material of the cone-shaped structure substrate is one or more of silicon, silicon dioxide, metal oxide, metal sulfide, metal phosphide, a thermosetting polymer, a thermoplastic polymer, a photocuring polymer, polydimethylsiloxane or a derivative of these materials.

A second objective of the present invention is to provide a construction method of the SERS substrate of the metal-modified semiconductor-based bionic compound eye bowl structure. The construction method includes the following steps:

(1) performing self-assembly on small balls with a diameter of 0.01-10 μm in a gas-liquid interface to obtain closely arranged single-layer balls;

(2) transferring the single-layer balls obtained in step (1) to a surface of a semiconductor precursor solution, assembling semiconductor films on the surfaces of the small balls below the liquid level in situ to obtain small balls with the semiconductor films attached to the lower surfaces;

(3) transferring the small balls with the semiconductor films attached to the lower surfaces obtained in step (2) to the surface of the cone-shaped structure substrate, and then removing the small balls to obtain an SERS substrate of a semiconductor-based bionic compound eye bowl structure; and (4) modifying a surface of the SERS substrate of the semiconductor-based bionic compound eye bowl structure obtained in step (3) with metal particles to obtain the SERS substrate of the metal-modified semiconductor-based bionic compound eye bowl structure.

Further, in step (4), the surface of the SERS substrate of the semiconductor-based bionic compound eye bowl structure is modified with the metal particles by a magnetron sputtering, physical vapor deposition, atomic layer deposition, chemical vapor deposition or precursor solution reaction method.

Further, a material of the small balls is one of silicon dioxide, polystyrene, polymethyl methacrylate, polyacrylic acid, polylactic acid, chitosan, gelatin, albumin, starch or a derivative of these materials.

Further, the small balls are removed by a solvent washing, solution washing, high-temperature calcination or dry etching method.

Further, a temperature of the high-temperature calcination is 200-900° C.

Further, gas of the dry etching is one or more of fluorine gas, oxygen gas, chlorine gas, argon gas, trifluoromethane, tetrafluoromethane, sulfur hexafluoride, boron trichloride, nitrogen trifluoride or silicon tetrahydride.

Further, in step (3), during transferring, the cone-shaped structure substrate is used for directly supporting the small balls with the semiconductor films attached to the lower surfaces from a solution.

A third objective of the present invention is to provide application of the SERS substrate of the metal-modified semiconductor-based bionic compound eye bowl structure to the field of Raman sensing.

Further, the application includes detection on harmful substances in water resources and food.

The present invention has the following beneficial effects:

The present invention is based on the multi-time interface self-assembly method. Firstly, the small ball template is constructed by using the gas-liquid interface assembly process. Then, the semiconductor bowl structure array is induced to be formed by the template by using the solid-liquid interface assembly process. Next, the semiconductor bowl is assembled to the surface of the pyramid-shaped cone to form the bionic compound eye structure by using the transfer process. Finally, the surface of the bionic compound eye structure is modified with one layer of uniformly distributed metal particles by the physical deposition method or the chemical deposition method, thereby forming the SERS substrate of the metal-modified semiconductor-based bionic compound eye bowl structure. The whole process is simple and easy to implement.

The SERS substrate of the present invention is a highly sensitive, renewable and reusable active substrate due to its special bionic structure and the special properties of a semiconductor material.

DETAILED DESCRIPTION OF THE INVENTION

Figure 1A:
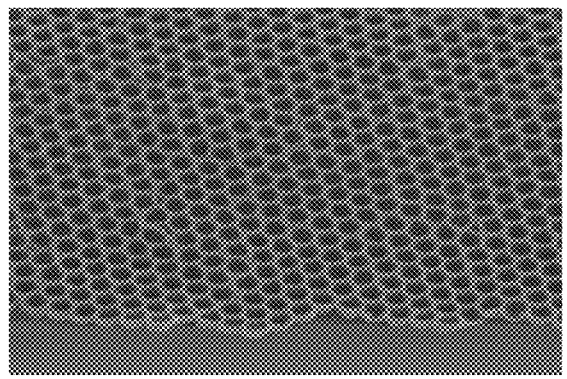
FIG. 1A is SEM diagram of a PPy nanobowl array structure.

The present invention is further illustrated hereafter in conjunction with specific embodiments to enable those skilled in the art to better understand and practice the present invention, but these embodiments are not intended to limit the present invention.

(1) Anti-Reflection Performance Test

The ultraviolet-visible reflection spectrum and the absorption spectrum of all samples were tested by a UV-3600plus ultraviolet-visible spectrophotometer of Shimadzu, Japan. The scanning speed was medium speed, and the test range was 200-1,500 nm.

(2) Micro-Morphology Test

The micro-morphology of the samples was observed by a scanning electron microscope, model S-4800, Hitachi Company, Japan. All the samples were not needed to be treated by metal spraying.

(3) Element Composition Test

The element composition and content of the samples were analyzed by an X photoelectron spectrometer cooperated with a field emission scanning electron microscope.

(4) X-Ray Diffractometer (XRD)

The crystal forms of the samples were analyzed by an XRD, model D8, Bruker AXS Co., Ltd, Germany. The test range was 20-80°.

(5) Raman Test

All the samples were subjected to Raman performance test by an inVia micro confocal Raman spectrometer, Renishaw Trading Co., Ltd, UK. Firstly, R6G was selected to be used as a probe molecule, and the concentration was $10^{-4}$ to $10^{-11}$ M. Then, 10 μL of R6G solutions with different concentrations were dripped to surfaces of SERS substrates. Finally, the above samples were subjected to Raman test.

Embodiment 1: Preparation of
Ag-NPs/PPy-NBs/Si—C Bionic Compound Eye
SERS Substrate 1 Preparation of Polystyrene (PS) Micro Balls Polystyrene (PS) micro balls were synthesized by an emulsion polymerization method. Styrene was taken and added into a three-neck flask. A proper amount of water was added. The three-neck flask was put into a 60° water bath kettle. Mechanical stirring was performed. After stirring for 1 h, an initiator was added. The initiator was a potassium persulfate solution. The reaction was performed for 24 h, and the PS micro balls with a diameter of 500 nm were successfully prepared. The obtained solution was washed with deionized water, centrifuged and dried for subsequent use.

2 Preparation of Polystyrene (PS) Ball Single-Layer Film Template

Firstly, a small amount of lauryl sodium sulfate was dripped into a petri dish containing deionized water to reduce surface tension. Then, 500 nm of PS balls were dripped onto on the liquid level in the petri dish. By using a capillary force generated by meniscuses among the PS balls at a gas-liquid interface, self-assembly was further performed to form hexagonal closely packed PS colloidal ball single-layer films, and a template was formed for use.

3 Preparation of Pyramid Array (Si—C)

Firstly, a silicon wafer was cut to a size of 1 cm×2 cm, and was then cleanly cleaned to remove impurities from the surface of the silicon wafer. Then, the clean silicon wafer was subjected to clear water modification. Finally, the treated silicon wafer was put into in a KOH solution, to perform an etching reaction at a temperature of 80° C. After the reaction for 20 min, a pyramid-shaped silicon cone structure (Si—C) was obtained.

4 Preparation of Single-Layer Polypyrrole Nanobowl/Silicon (PPy-NBs/Si—C) Composite Material Firstly, 50 mL of a pyrrole (Py) solution and 50 mL of a ferric trichloride ($FeCl_3$) solution were subjected to ultrasonic blending. Then, the single-layer film template of the PS colloidal balls with the diameter of 500 nm obtained in the previous step was transferred into the blended solution to perform an assembly reaction for 1 h at room temperature. The PS small balls with the polypyrrole (PPy) films attached to the lower surfaces were successfully obtained. Then, the PS small balls with the PPy films attached to the lower surfaces were transferred to the surface of the pyramid silicon cone. Finally, the PS small balls were removed by ethanol to obtain the polypyrrole nanobowl/silicon (PPy-NBs/Si—C) composite material.

5 Preparation of Silver/Polypyrrole Nanobowl/Silicon (Ag-NPs/PPy-NBs/Si—C) Composite Material (1) Preparation of sodium citrate solution: Sodium citrate ($Na_3C_6H_5O_7 \cdot 2H_2O$, 1.0 g) was dissolved in 99 mL of water to be prepared into a 1% sodium citrate water solution.

(2) Preparation of silver sol solution: Silver nitrate ($AgNO_3$, 0.1 mmol) was dissolved in 100 mL of deionized water to be prepared into a silver nitrate water solution. Under the mechanical stirring condition, the temperature was raised to enable the solution to boil. Then, the prepared sodium citrate water solution was added for reaction for 60 min to obtain a silver sol solution.

(3) Preparation of Ag-NPs/PPy-NBs/Si—C: The above polypyrrole nanobowl/silicon (PPy-NBs/Si—C) samples were put into the silver sol solution to deposit Ag-NPs. A silver/polypyrrole nanobowl/silicon (Ag-NPs/PPy-NBs/Si—C) composite material was obtained.

Embodiment 2: Preparation of Ag-NPs/PPy-NBs/TiO$_2$—C Bionic Compound Eye SERS Substrate 1 Preparation of Polystyrene (PS) Micro Balls Polystyrene (PS) micro balls were synthesized by an emulsion polymerization method. Styrene was taken and added into a three-neck flask. A proper amount of water was added. The three-neck flask was put into a 60° water bath kettle. Mechanical stirring was performed. After stirring for 1 h, an initiator was added. The initiator was a potassium persulfate solution. The reaction was performed for 24 h, and the PS micro balls were successfully prepared. The obtained solution was washed with deionized water, centrifuged and dried for subsequent use.

2 Preparation of Polystyrene (PS) Ball Single-Layer Film Template

Firstly, a small amount of lauryl sodium sulfate was dripped into a petri dish containing deionized water to reduce surface tension. Then, 500 nm of PS balls were dripped onto on the liquid level in the petri dish. By using a capillary force generated by meniscuses among the PS balls at a gas-liquid interface, self-assembly was further performed to form hexagonal closely packed PS colloidal ball single-layer films, and a template was formed for use.

3 Preparation of TiO$_2$ Pyramid Array (TiO$_2$—C)

(1) Preparation of Pyramid Silicon Cone Array

Firstly, a silicon wafer was cut to a size of 1 cm×2 cm, and was then cleanly cleaned to remove impurities from the surface of the silicon wafer. Then, the clean silicon wafer was subjected to clear water modification. Finally, the treated silicon wafer was put into in a KOH solution, to perform an etching reaction at a temperature of 80° C. After the reaction for 20 min, a pyramid-shaped silicon cone structure was obtained.

(2) Preparation of PDMS Soft Template

The etched sample (1 cm×2 cm) with a pyramid structure was cleaned. Then, the silicon wafer with a silicon cone structure was coated with uniformly stirred PDMS prepolymers. Curing was performed for 3 h in a baking oven. After cooling, the PDMS was separated from the silicon wafer to obtain a recessed pyramid-shaped structure template.

(3) Preparation of TiO$_2$ Pyramid Cone-Shaped Structure

Firstly, 60 µL of TiO$_2$ sol was dripped on the substrate, and a cone surface of the PDMS template was immediately spread on the surface of the substrate attached to TiO$_2$. Then, still standing was performed for 24 h in a 100° C. environment. The PDMS template was separated from the substrate to obtain a pyramid-shaped TiO$_2$ structure. Finally, the substrate with the TiO$_2$ structure was calcined for 3 h in a tubular muffle furnace at 450° C. reached through temperature rise at a temperature rise speed of 1° C./min. An anatase type TiO$_2$ pyramid-shaped structure (TiO$_2$—C) with a high crystallinity degree was obtained.

4 Preparation of Single-Layer Polypyrrole Nanobowl/TiO$_2$ Pyramid Cone (PPy-NBs/TiO$_2$—C) Composite Material Firstly, 50 mL of a pyrrole (Py) solution and 50 mL of a ferric trichloride (FeCl$_3$) solution were subjected to ultrasonic blending. Then, the single-layer film template of the PS colloidal balls with the diameter of 500 nm obtained in the previous step was transferred into the blended solution to perform an assembly reaction for 1 h at room temperature. The PS small balls with the polypyrrole (PPy) films attached to the lower surfaces were successfully obtained. Then, the PS small balls with the PPy films attached to the lower surfaces were transferred to the surface of the TiO$_2$ pyramid cone. Finally, the PS small balls were removed by ethanol to obtain the polypyrrole nanobowl/TiO$_2$ pyramid cone (PPy-NBs/TiO$_2$—C) composite material.

5 Preparation of Silver/Polypyrrole Nanobowl/TiO$_2$ Pyramid Cone (Ag-NPs/PPy-NBs/TiO$_2$—C) Composite Material (1) Preparation of sodium citrate solution: Sodium citrate ($Na_3C_6H_5O_7 \cdot 2H_2O$, 1.0 g) was dissolved in 99 mL of water to be prepared into a 1% sodium citrate water solution.

(2) Preparation of silver sol solution: Silver nitrate ($AgNO_3$, 0.1 mmol) was dissolved in 100 mL of deionized water to be prepared into a silver nitrate water solution. Under the mechanical stirring condition, the temperature was raised to enable the solution to boil. Then, the prepared sodium citrate water solution was added for reaction for 60 min to obtain a silver sol solution.

(3) Preparation of Ag-NPs/PPy-NBs/TiO$_2$—C: The above polypyrrole nanobowl/TiO$_2$ pyramid cone (PPy-NBs/TiO$_2$—C) samples were put into the silver sol solution to deposit Ag-NPs. The silver/polypyrrole nanobowl/TiO$_2$ pyramid cone (Ag-NPs/PPy-NBs/TiO$_2$—C) composite material was obtained.

Figure 1B:
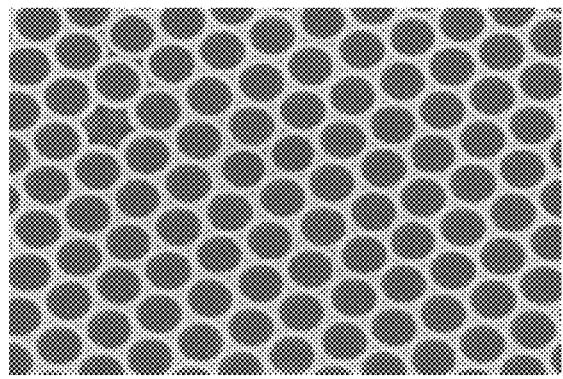
FIG. 1B is an enlarged SEM diagram of a PPy nanobowl array structure.
Figure 1C:
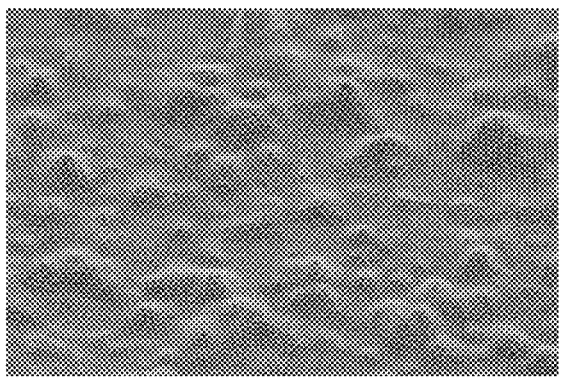
FIG. 1C is a SEM diagram of a $TiO_2$ pyramid cone composite PPy nanobowl (PPy/$TiO_2$—C)
Figure 1D:
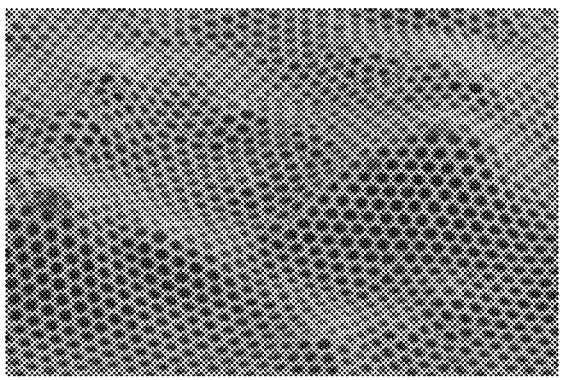
FIG. 1D is an enlarged SEM diagram of a $TiO_2$ pyramid cone composite PPy nanobowl (PPy/$TiO_2$—C)
Figure 2:
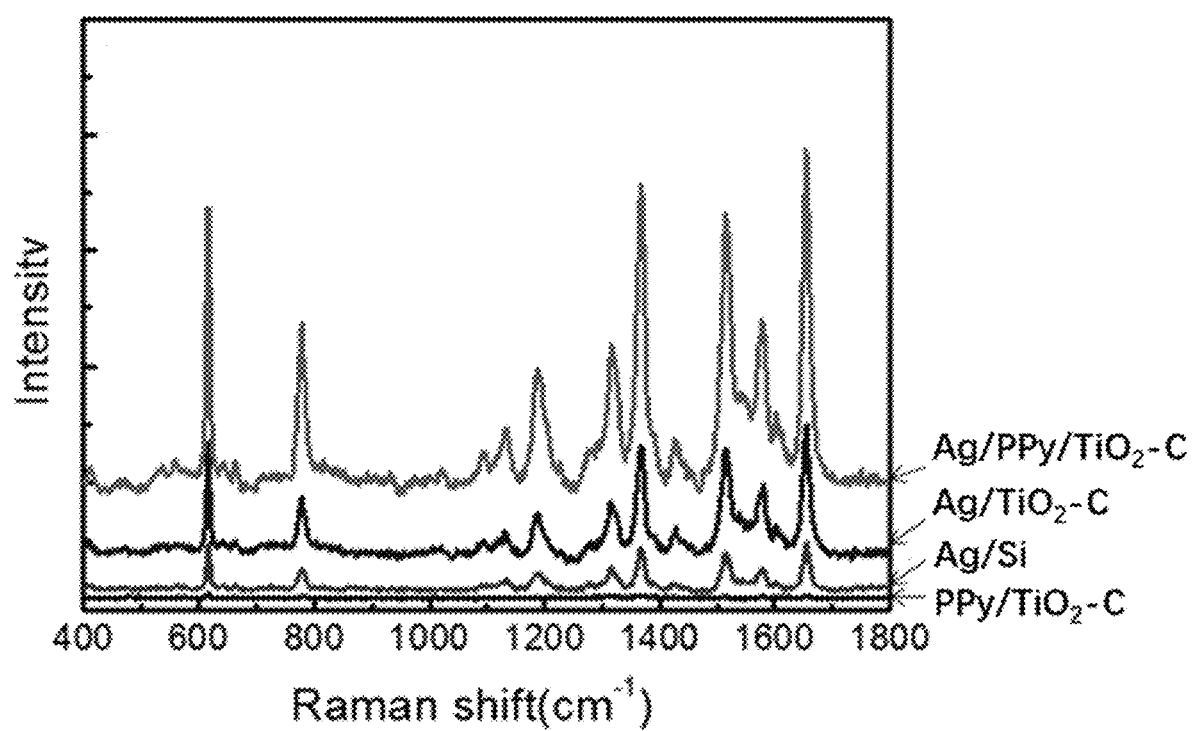
FIG. 2 is a Raman spectrum of R6G on different SERS substrates (PPy/$TiO_2$—C, Ag/Si, Ag/$TiO_2$—C, and Ag/PPy/$TiO_2$—C).

Embodiment 3: Micro-Morphology of Ag-NPs/PPy-NBs/TiO$_2$—C Bionic Compound Eye SERS Substrate The morphologies of the PPy nanobowl array structure and the TiO$_2$ cone-shaped structure composite PPy nanobowl structure in the process of Embodiment 2 are as shown in FIG. 1. The PPy nanobowl array structure could be formed after PS balls were dissolved. As shown in FIG. 1A and FIG. 1B, the PPy nanobowl array formed after the PS micro balls were removed had smooth surfaces, a uniform diameter, regular edges and high quality. In the PS micro ball array template, six micro balls surrounded one, and PPy polymers in adhesion positions among the PS micro balls and gap positions among the micro balls could not be coated, so that a porous structure was formed. On one hand, this porous structure provided a passage for liquid circulation, and was beneficial to its liquid phase catalysis. On the other hand, the porous structure was beneficial to formation of Ag NPs "hot spots". The TiO$_2$ cone-shaped structure composite PPy nanobowl structure is as shown in FIG. 1C and FIG. 1D. It could be seen that the PPy nanobowl array closely coated the surfaces of cones for a large area, and a fluctuation state was maintained along with the sizes of the cone structures. Therefore, the roughness of a whole structure was increased. On one hand, the result conformed to an effective medium theory and improved the light absorption performance of the structure surface. On the other hand, the formed nanobowl array structure provided a good three-dimensional structure when being used as a Raman enhancement substrate.

Embodiment 4: Raman Signal of Ag-NPs/PPy-NBs/TiO$_2$—C Bionic Compound Eye SERS Substrate In order to demonstrate that Ag-NPs/PPy-NBs/TiO$_2$—C bionic compound eye SERS substrate in Embodiment 2 had the advantage of improving SERS signals, Ag-NPs was respectively deposited on a silicon (Si) surface and the pyramid-shaped structure with TiO$_2$ to form Ag/Si and Ag/TiO$_2$—C composite substrates under the same deposition conditions. Then, R6G was used as a probe molecule to study the SERS performance on different substrates (Ag/Si, Ag/TiO$_2$—C, and Ag/PPy/TiO$_2$—C). From the Raman spectrum 2, it could be seen that almost no Raman signal was on the PPy/TiO$_2$—C surface. However, after the Ag-NPs deposition on the Si surface, the Raman signal was enhanced to a certain degree. The Raman signal on the Ag/PPy/TiO$_2$—C substrate was obviously higher than that on Ag/Si and Ag/TiO$_2$—C.

Embodiment 5: Photocatalysis Capability and Reusability of Ag-NPs/PPy-NBs/TiO$_2$—C Bionic Compound Eye SERS Substrate The photocatalysis capability of the SERS substrate obtained in Embodiment 2 was tested. The photocatalysis performance of the sample was tested by a TU-1901 dual-beam spectrophotometer, Beijing Purkinje General Instrument Co., Ltd. A $10^{-5}$ M Rhodamine 6G (Rh6G) probe molecule was used as a photodegradation study object. Simulated sun irradiation was used as a catalysis light source environment. A test wavelength range was 200-800 nm. Through study, it was discovered that after light illumination for 2 h, the Rhodamine 6G (Rh6G) probe molecule on the surface of the SERS substrate was completely degraded, and the corresponding Raman signal completely disappeared. Therefore, it could be shown that this SERS substrate could be efficiently and repeatedly used.

Embodiment 6: Application of Ag-NPs/PPy-NBs/TiO$_2$—C Bionic Compound Eye SERS Substrate to Detection on Furazolidone Residue in Fruits and Vegetables Acetone solutions containing 0.01, 0.05, 0.1, 0.5, 1 and 1.5 mg/mL furazolidone were respectively prepared. The SERS substrates prepared in Embodiment 2 were respectively soaked in the solutions. After soaking for 1 h, molecules to be tested were enabled to be adsorbed on the surfaces of the SERS substrates. The SERS substrates were taken out and dried, and were scanned by laser of a Raman spectrometer to obtain a surface enhanced Raman spectrogram of the solution at each concentration gradient. Characteristic peaks of the furazolidone were analyzed, and a standard curve between the Raman signal intensity and the corresponding furazolidone concentration was further built.

5 g of a vegetable sample was accurately weighed, was sufficiently crushed and was put into a centrifuge tube. 20 mL of acetone was added for extraction. After filtration, the volume was regulated to 20 mL. Then, the SERS substrate prepared in Embodiment 2 was soaked in the solution. After soaking for 1 h, molecules to be detected were enabled to be adsorbed on the surface of the SERS substrate. The SERS substrate was taken out and dried, and was scanned by laser of a Raman spectrometer to obtain a surface enhanced Raman spectrogram thereof. In combination with a standard curve, the furazolidone content in the sample was obtained and was 0.064 mg/g.

The above-mentioned embodiments are merely exemplary embodiments for fully illustrating the present invention, and the protection scope of the present invention is not limited thereto. The equivalent substitution or change made by those skilled in the art on the basis of the present invention all falls within the protection scope of the present invention. The protection scope of the present invention is defined by the claims appended hereto.

What is claimed is:

1. A construction method of an SERS substrate of a metal-modified semiconductor-based bionic compound eye bowl structure, comprising the following steps:
    (1) performing self-assembly on small balls with a diameter of 0.01-10 μm in a gas-liquid interface to obtain closely arranged single-layer balls;
    (2) transferring the single-layer balls obtained in step (1) to a surface of a semiconductor precursor solution, assembling semiconductor films on surfaces of the small balls below liquid level in situ to obtain small balls with the semiconductor films attached to lower surfaces;
    (3) transferring the small balls with the semiconductor films attached to the lower surfaces obtained in step (2) to surface of a cone-shaped structure substrate, and then removing the small balls to obtain an SERS substrate of a semiconductor-based bionic compound eye bowl structure; and
    (4) modifying a surface of the SERS substrate of the semiconductor-based bionic compound eye bowl structure obtained in step (3) with metal particles to obtain the SERS substrate of the metal-modified semiconductor-based bionic compound eye bowl structure that consists of cone-shaped structure substrates and semiconductor-based bionic compound eye bowl structures on surfaces of the cone-shaped structure substrates;
    wherein a height of the cone-shaped structure substrate is 1-100 μm, and a particle size of the metal particles is 1-100 nm; and
    a material of the semiconductor films is silicon, metal oxide, metal sulfide, metal phosphide or a conductive polymer.

2. The construction method according to claim 1, wherein a material of the metal particles is one or more of gold, silver, palladium, platinum, copper, lithium or sodium.

3. The construction method according to claim 1, wherein a material of the cone-shaped structure substrate is one or more of silicon, silicon dioxide, metal oxide, metal sulfide, metal phosphide, a thermosetting polymer, a thermoplastic polymer, a photocuring polymer, polydimethylsiloxane or a derivative of these materials.

4. The construction method according to claim 1, wherein in step (4), the surface of the SERS substrate of the semiconductor-based bionic compound eye bowl structure are modified with the metal particles by a magnetron sputtering, physical vapor deposition, atomic layer deposition, chemical vapor deposition or precursor solution reaction method.

5. The construction method according to claim 1, wherein a material of the small balls is one of silicon dioxide, polystyrene, polymethyl methacrylate, polyacrylic acid, polylactic acid, chitosan, gelatin, albumin, starch or a derivative of these materials.

6. The construction method according to claim 1, wherein the small balls are removed by a solvent washing, solution washing, high-temperature calcination or dry etching method.

7. A method for detecting a Raman signal comprising a step for measuring the Raman signal on a subject in need with the SERS substrate of the metal-modified semiconductor-based bionic compound eye bowl structure of claim 1.

8. The method according to claim 7, wherein the subject contains harmful substances.

* * * * *